(12) United States Patent
Wang (10) Patent No.: US 8,225,680 B2
(45) Date of Patent: Jul. 24, 2012

(54) WIPE SAMPLING DEVICE OF RADIOACTIVE CONTAMINANTS ON SURFACE OF SPENT NUCLEAR FUEL STORAGE CANISTER

(75) Inventor: Wen-Hwa Wang, Longtan Township, Taoyuan County (TW)

(73) Assignee: Atomic Energy Council-Institute of Nuclear Energy Research, Taoyuan County (TW)

( * ) Notice: Subject to any disclaimer, the term of this patent is extended or adjusted under 35 U.S.C. 154(b) by 648 days.

(21) Appl. No.: 12/348,368

(22) Filed: Jan. 5, 2009

(65) Prior Publication Data

US 2010/0170351 A1 Jul. 8, 2010

(51) Int. Cl.
*G01N 1/04* (2006.01)
(52) U.S. Cl. ............ 73/864.71; 73/863; 435/30
(58) Field of Classification Search ............ 73/864.71, 73/863; 435/30
See application file for complete search history.

(56) References Cited

U.S. PATENT DOCUMENTS

| | | | | |
|---|---|---|---|---|
| 3,684,660 A * | 8/1972 | Kereluk et al. | ............ | 435/305.1 |
| 4,014,746 A * | 3/1977 | Greenspan | ............ | 435/243 |
| 4,059,404 A * | 11/1977 | Schuster et al. | ............ | 600/573 |
| 4,223,093 A * | 9/1980 | Newman et al. | ............ | 600/572 |
| 6,248,294 B1 * | 6/2001 | Nason | ............ | 422/411 |
| 6,383,804 B1 * | 5/2002 | Ward et al. | ............ | 435/309.1 |
| 6,548,018 B2 * | 4/2003 | DiCesare et al. | ............ | 422/52 |
| 6,653,147 B2 * | 11/2003 | DiCesare | ............ | 436/172 |
| 6,881,554 B2 * | 4/2005 | DiCesare et al. | ............ | 435/30 |
| 6,887,681 B2 * | 5/2005 | DiCesare et al. | ............ | 435/30 |
| 6,991,898 B2 * | 1/2006 | O'Connor | ............ | 435/4 |
| 7,060,223 B2 * | 6/2006 | DiCesare et al. | ............ | 422/52 |
| 7,485,262 B2 * | 2/2009 | DiCesare et al. | ............ | 422/404 |
| 2001/0046687 A1 * | 11/2001 | DiCesare | ............ | 435/8 |
| 2002/0001539 A1 * | 1/2002 | DiCesare et al. | ............ | 422/52 |
| 2002/0001822 A1 * | 1/2002 | DiCesare | ............ | 435/40.5 |
| 2002/0018986 A1 * | 2/2002 | DiCesare | ............ | 435/4 |
| 2002/0187076 A1 * | 12/2002 | DiCesare et al. | ............ | 422/99 |
| 2003/0109057 A1 * | 6/2003 | DiCesare et al. | ............ | 436/172 |
| 2003/0129765 A1 * | 7/2003 | DiCesare et al. | ............ | 436/172 |
| 2003/0186458 A1 * | 10/2003 | DiCesare et al. | ............ | 436/172 |
| 2005/0084842 A1 * | 4/2005 | O'Connor | ............ | 435/4 |
| 2005/0136238 A1 * | 6/2005 | Lindsay et al. | ............ | 428/304.4 |

\* cited by examiner

*Primary Examiner* — Hezron E Williams
*Assistant Examiner* — Rodney T Frank
(74) *Attorney, Agent, or Firm* — Ming Chow; Sinorica, LLC

(57) ABSTRACT

A wipe sampling device of radioactive contaminants on surface of spent nuclear fuel storage canisters is revealed. The wipe sampling device of radioactive contaminants takes samples from the storage canister to get at least one sample for monitoring radioactive contamination on the surface of the canister. The sampling device mainly includes a sample stick and a tube. The sample stick disposed in the tube is used to take samples from the surface of the canister. The wipe sampling device of radioactive contaminants on surface of the canister provides an effective sampling method for remote detection of canister contamination and ensures accuracy and representation of the detection results.

16 Claims, 8 Drawing Sheets

Fig.7

WIPE SAMPLING DEVICE OF RADIOACTIVE CONTAMINANTS ON SURFACE OF SPENT NUCLEAR FUEL STORAGE CANISTER

BACKGROUND OF THE INVENTION

1. Field of Invention

The present invention relates to a wipe sampling device of contaminants, especially to a wipe sampling device of radioactive contaminants on surface of storage canisters.

2. Description of Related Art

There are two kinds of method to storage the spent nuclear fuels. One is wet storage and the other is dry storage. The wet storage is to store spent nuclear fuel in spent fuel (water-filled) pools near nuclear facility while the dry storage means there is no water in a storage device or shield device. However, the fuel pools in use are difficult to be modified and the storage space is limited. Thus when the spaces of the fuel pool are approaching full, the spent fuels have to be transferred to dry storage container so as to make room for the fuel pools. Before being transferred to dry storage, the spent nuclear fuels are placed in canisters that are sealed, vacuumed and filled with inert gas for stability. Metal or concrete casks are located outside of the canisters for shield. During transferring processes, radioactive contamination on the surface of the canister will be sampled after the canister being put into a storage cask. A gap between the canister and the storage cask is only 2 centimeter and the length of the canister is about 5 meters so that radiation workers are unable to contact, wipe and get sample for measurement. There is no effective sampling device available now and the data obtained is neither representative nor accurate. Thus there is a need to provide a wipe sampling device of radioactive contaminants on surface of spent nuclear fuel canister loaded in storage cask.

SUMMARY OF THE INVENTION

It is the primary object of the present invention to provide an effective wipe sampling device of radioactive contaminants on surface of spent nuclear fuel canisters that ensures accuracy and representation of the radioactive contamination on surface of canisters through a sampling way with constant sampling area and exerting a constant force.

In order to achieve above object, a sampling device of the present invention is used to get at least one sample from the cask for monitoring the surface radioactive contamination per unit area. The sampling device mainly consists of a sample stick and a tube. The sample stick is disposed in the tube. The sample stick takes samples from a certain area on the surface of the cask and exerts a constant force on the sampled area during the sampling.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein.

DETAILED DESCRIPTION OF THE PREFERRED EMBODIMENT

Figure 1A:
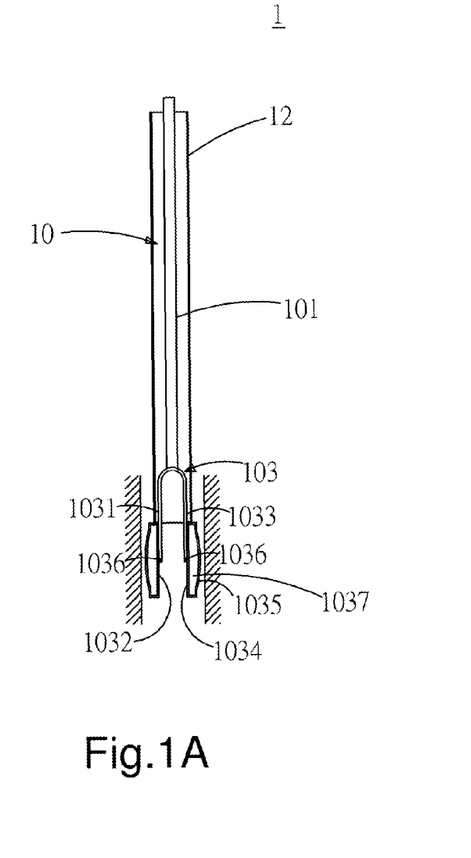
FIG. 1A is a schematic drawing showing structure of an embodiment according to the present invention.
Figure 1B:
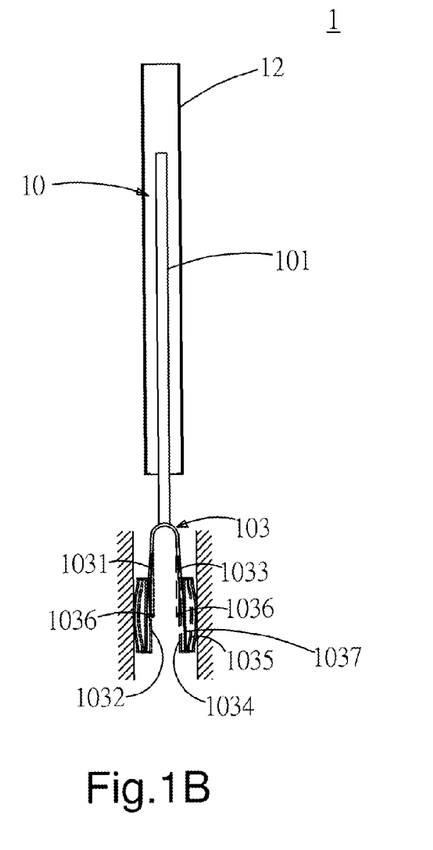
FIG. 1B is a use status of an embodiment according to the present invention.

Refer from FIG. 1A to FIG. 1B, schematic drawings show structure and use of an embodiment of the present invention. A wipe sampling device 1 of radioactive contaminants on surface of spent nuclear fuel storage canisters according to the present invention takes at least one sample from a canister for monitoring radioactive contamination on surface of the canister. The wipe sampling device 1 includes a sample stick 10 and a tube 12. The sample stick 10 is disposed in the tube 12. The sample stick 10 consists of a handle 101 and a U-shaped sampling part 103. The U-shaped sampling part 103 is disposed on one end of the handle 101 and is made of elastic and rigid material such as metal springs. The U-shaped sampling part 103 comprises a first sampling rack 1031 and a second sampling rack 1033, both are disposed with a sampling paper 1035.

In order to fix the sampling paper 1035 on the first sampling rack 1031 as well as the second sampling rack 1033, the device further includes a first fixed rack 1032 and a second fixed rack 1034. The first fixed rack 1032 and the second fixed rack 1034 are used for fixing the sampling paper 1035.

In order to make the sampling paper 1035 wipe along the surface of the canister, a rotation shaft 1036 is disposed between the first sampling rack 1031 and the first fixed rack 1032 as well as between the second sampling rack 1033 and the second fixed rack 1034. Moreover, an elastic member 1037 is arranged between the sampling paper 1035 and the first fixed rack 1032/second fixed rack 1034 so that the sampling paper 1035 is pressured to attach firmly on the surface of the canister.

In use, the tube 12 of the wipe sampling device 1 of the present invention is insert into the gap between the canister and the cask. The sample stick 10 is disposed in the tube 12 and part of the U-shaped sampling part 103 of the sample stick 10 is in the tube 12. While performing contamination detection, the sample stick 10 is released and the U-shaped sampling part 103 extends out of the tube 12. Because the U-shaped sampling part 103 is made of elastic and rigid material, the sampling paper 1035 is pop out and attached closely to the surface of the canister for taking a sample. The length of the sample stick 10 of the wipe sampling device 1 is fixed. Thus the sampling area of the sampling paper 1035 can be fixed so as to get representative sampled data.

Figure 2A:
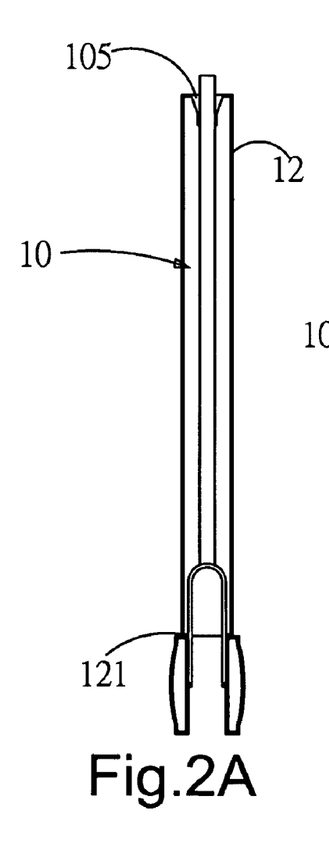
FIG. 2A is a schematic drawing showing structure of another embodiment according to the present invention.
Figure 2B:
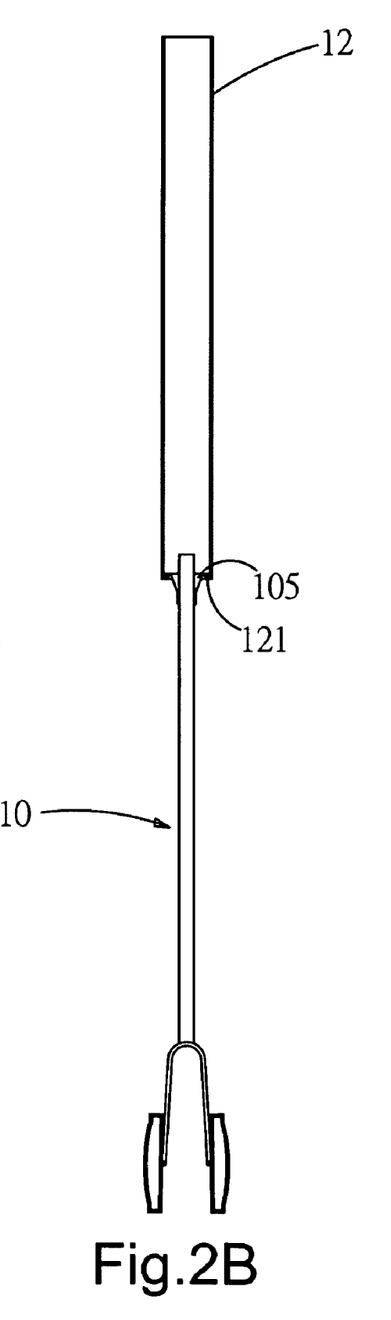
FIG. 2B is a use status of another embodiment according to the present invention.

Refer to FIG. 2A & FIG. 2B, schematic drawings showing structure and use of another embodiment are disclosed. The difference between this embodiment and the above one in FIG. A is in that a stopper 121 is disposed on a tube 12 and a sample stick 10 is disposed with a projecting member 105 for controlling traveling distance of the sample stick 10 and preventing the sample stick 10 from falling apart with the tube 12. When the sample stick 10 is traveling, the projecting member 105 rests against the stopper 121 and the sample stick 10 is stopped.

Figure 3A:
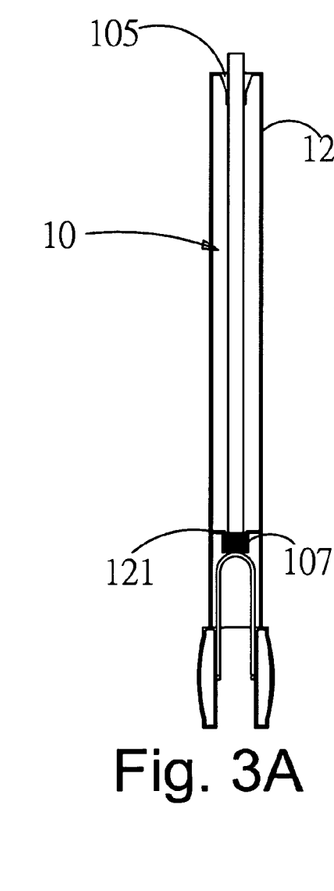
FIG. 3A is a schematic drawing showing structure of a further embodiment according to the present invention.
Figure 3B:
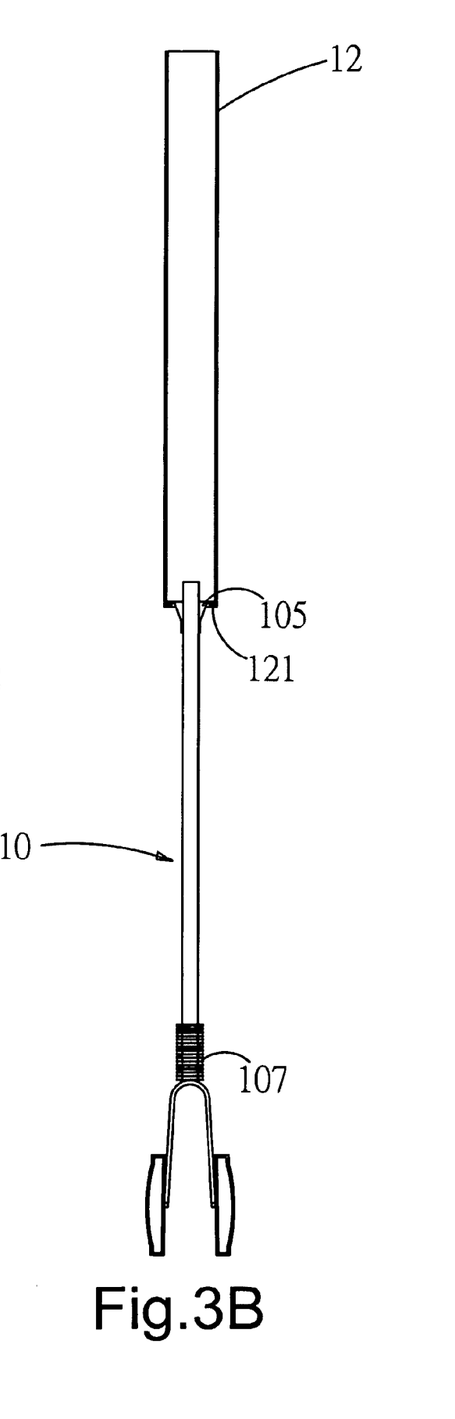
FIG. 3B is a use status of a further embodiment according to the present invention.

Refer to FIG. 3A & FIG. 3B, a further embodiment is revealed. As shown in figure, in order to prevent a friction force generated between the sampling paper 1035 and the surface of the canister and the sample stick 10 can't travel smoothly, an external force is applied to make the sample stick 10 travel smoothly. The sample stick 10 is disposed with a spring 107 sleeved around the handle 101 and located around the U-shaped sampling part 103. When the sample stick 10 is in the tube 12, the spring 107 is compressed by the stopper 121. When the sample stick 10 is released, the spring 107 is also released to generate a power that projects the sample stick 10 out of the tube 12.

Figure 4:
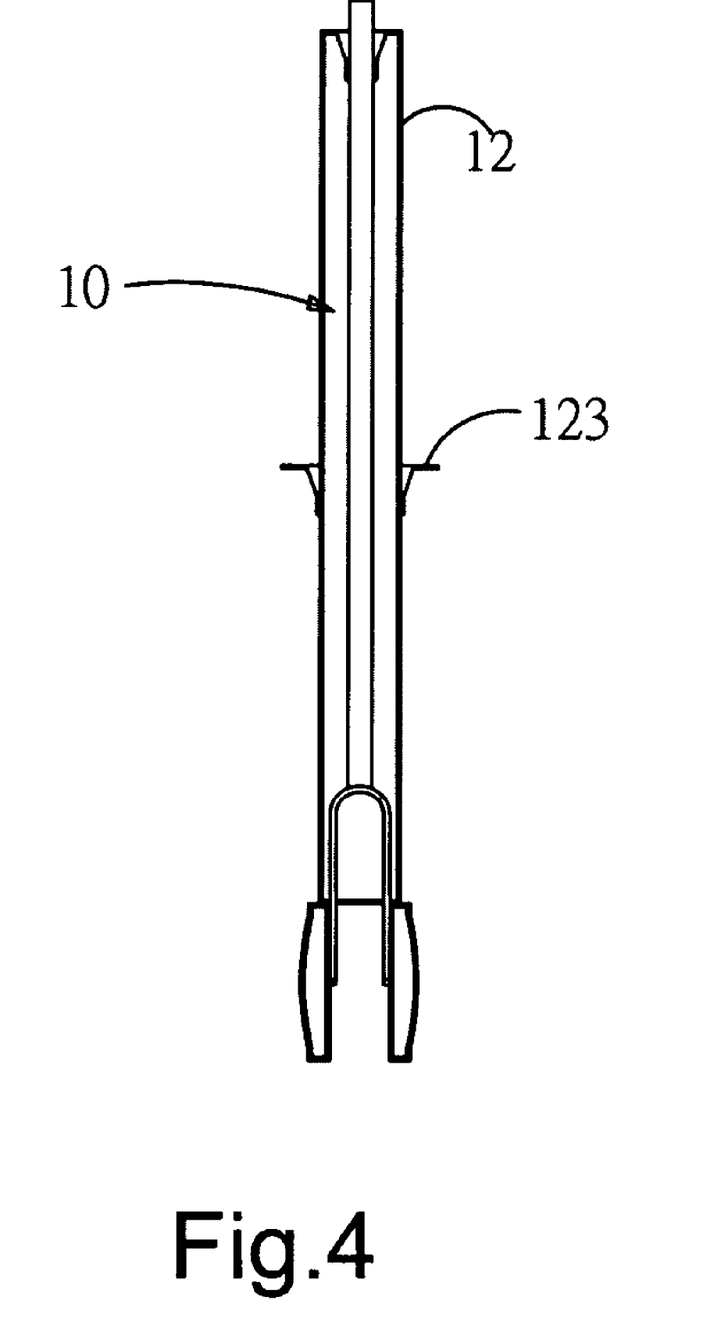
FIG. 4 is a schematic drawing showing structure of a further embodiment according to the present invention.

Refer to FIG. 4, a further embodiment is disclosed. The difference between this embodiment and the above one is in that a fixing ring 123 is disposed on the tube 12 for easy installation of the wipe sampling device 1 between the canister and the cask. The tube 12 is fixed between the canister and the cask by means of the fixing ring 123.

Figure 5:
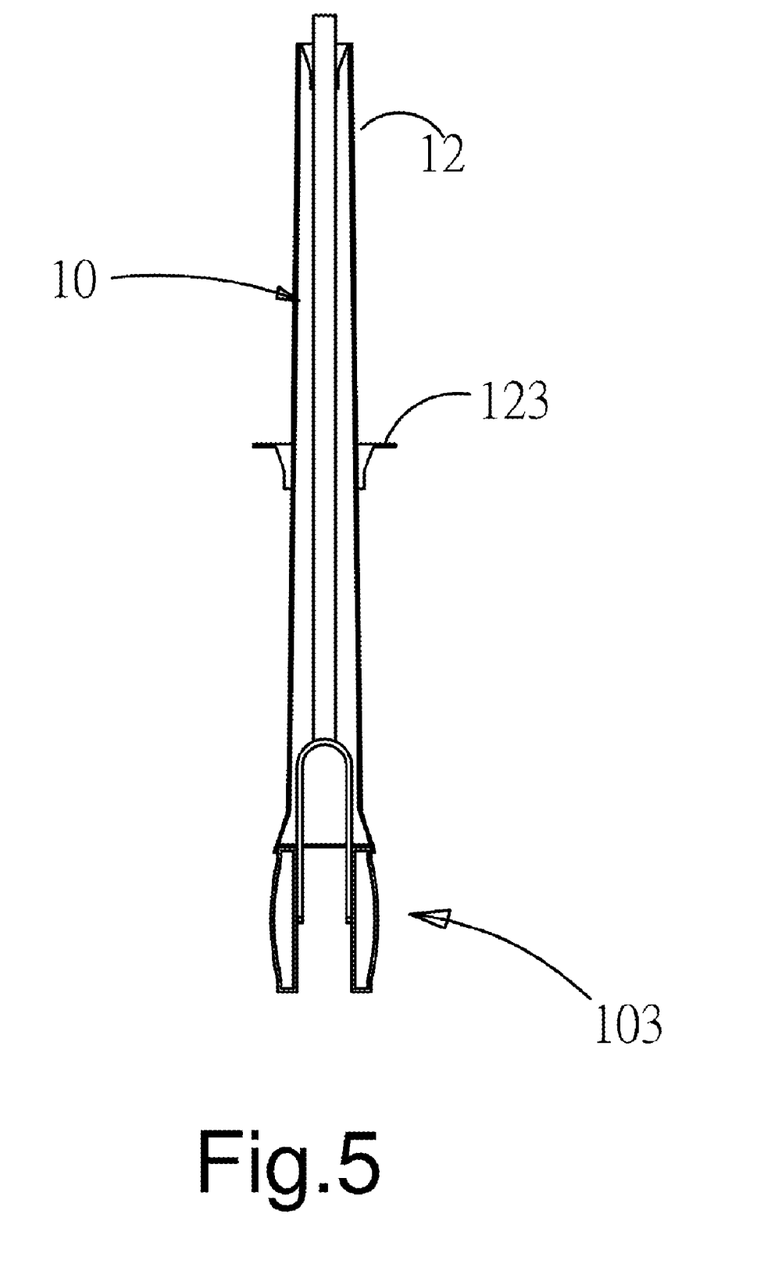
FIG. 5 is a schematic drawing showing structure of a further embodiment according to the present invention.

Refer to FIG. 5, a further embodiment is revealed. The difference between this embodiment and the above one is in that diameter of an opening on one end of the tube 12 near the U-shaped sampling part 103 is larger than that of an opening on the other end of the tube 12 for convenience of receiving the U-shaped sampling part 103 of the sample stick 10 into the tube 12. And the opening on the end of the tube 12 near the U-shaped sampling part 103 is tapered (getting narrower).

Figure 6:
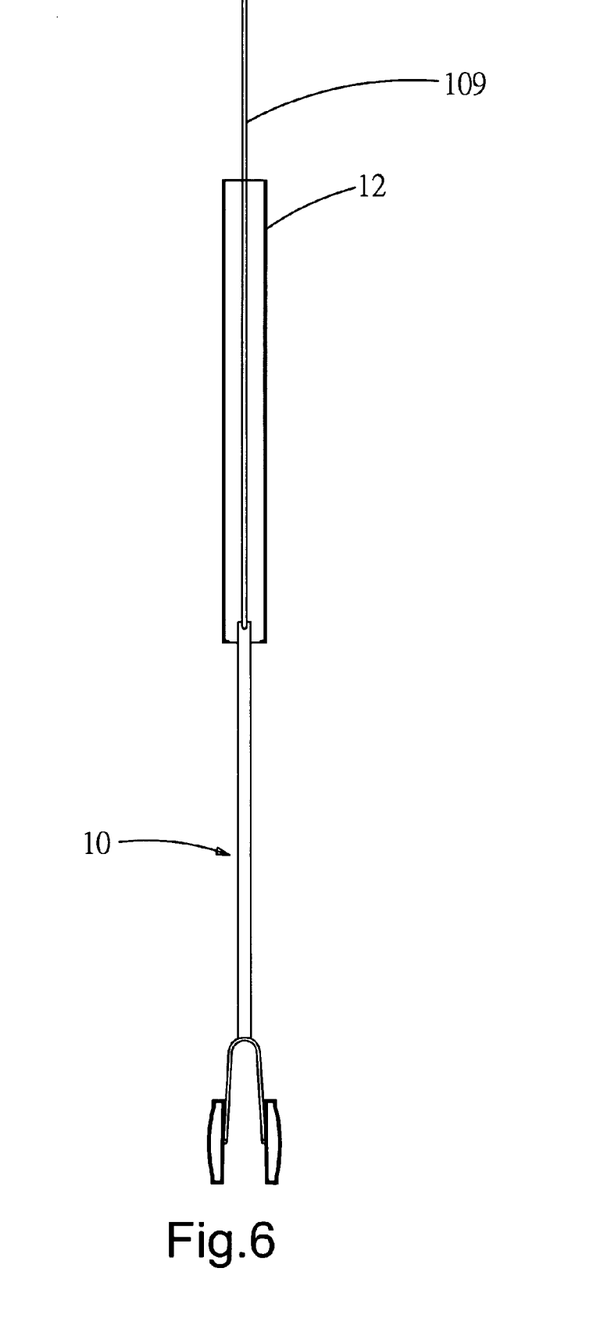
FIG. 6 is a schematic drawing showing structure of a further embodiment according to the present invention.

Refer to FIG. 6, a further embodiment is revealed. As shown in figure, the difference between this embodiment and the above one is in that a string 109 is disposed on one end of the sample stick 10, opposite to the end near the U-shaped sampling part 103 for convenience of pulling the sample stick 10 back. While pulling back the string 109, the sample stick 10 is also pulled back and received into the tube 12.

Figure 7:
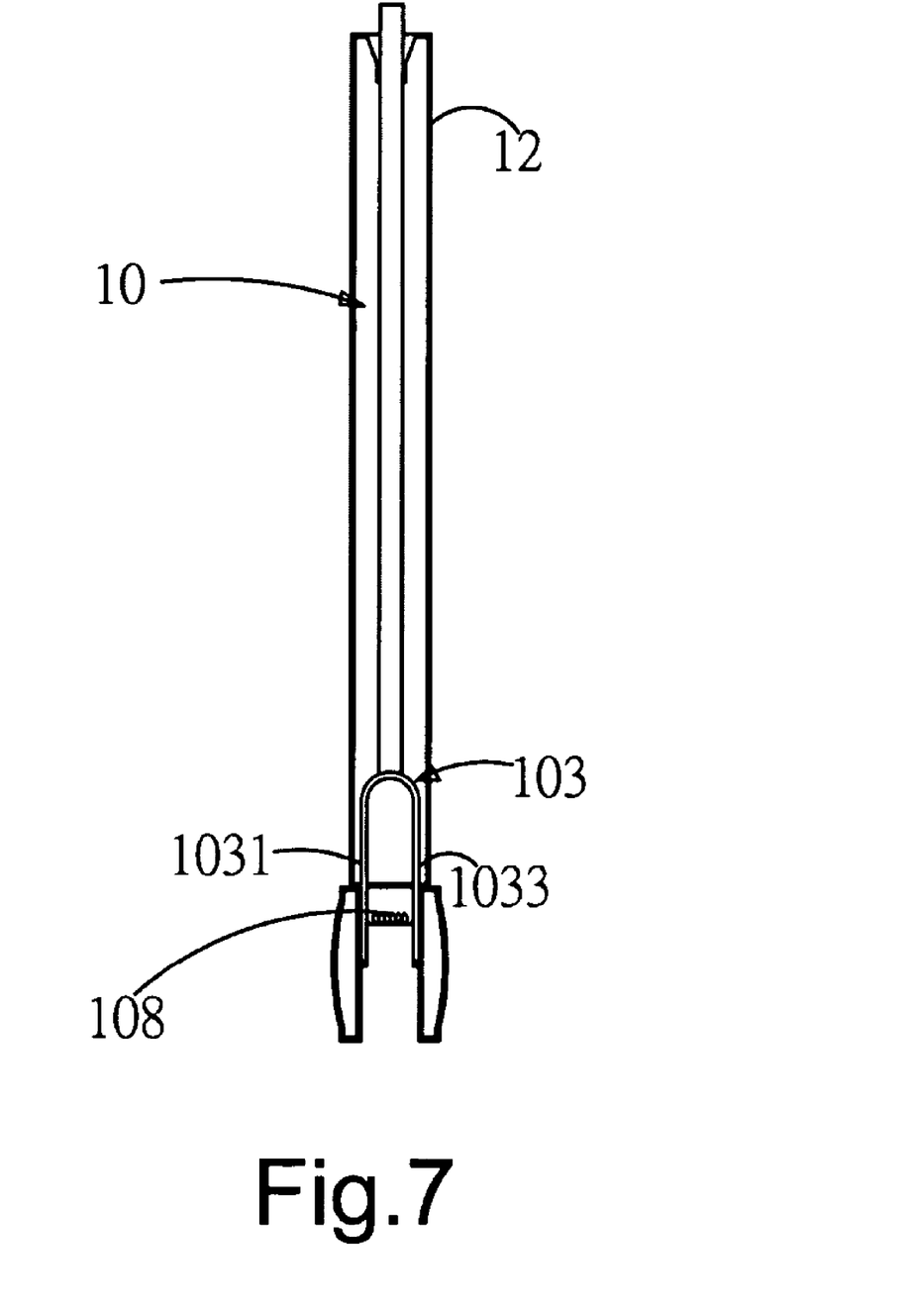
FIG. 7 is a schematic drawing showing structure of a further embodiment according to the present invention.

Refer to FIG. 7, a further embodiment is revealed. As shown in figure, the difference between this embodiment and the above one is in that a spring 108 is disposed between the first sampling rack 1031 and the second sampling rack 1033 so as to make the sampling paper 1035 attach more closely to the surface of the canister. By elastic force of the spring 108, the first sampling rack 1031 and the second sampling rack 1033 are installed and supported.

Figure 8:
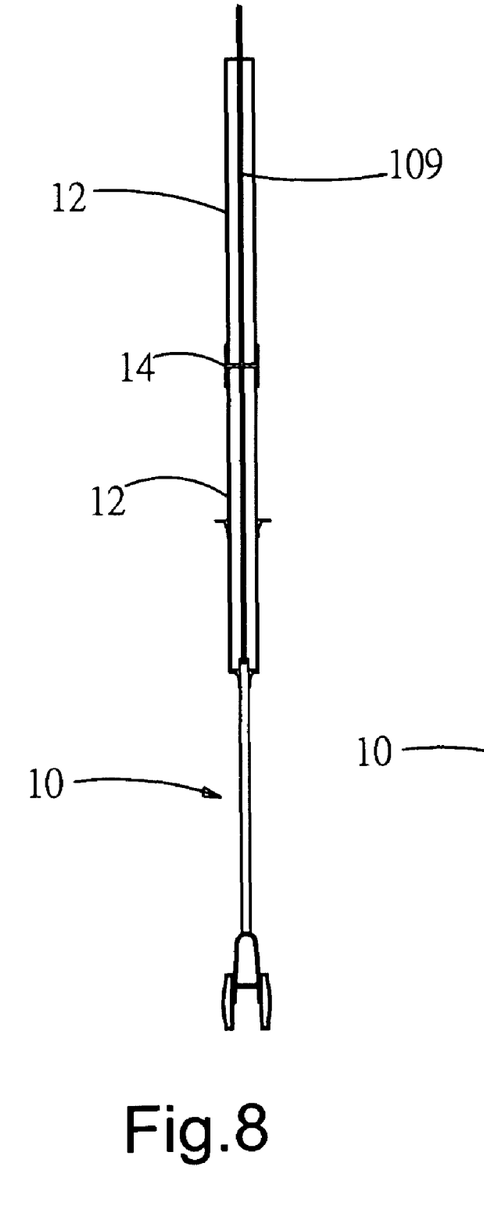
FIG. 8 is a schematic drawing showing structure of a further embodiment according to the present invention.

Refer to FIG. 8, a further embodiment is revealed. As shown in figure, this embodiment and the above one both have a single tube 12. The difference between this embodiment and the above one is in that the tube 12 is further connected with at least one other tube 12 for increasing length of the tube 12. Thus not only the length of the tube 12 is increased, the tube 12 is also easy to be assembled, detached and stored. The tubes 12 are connected with each other by a connector 14 so as to achieve fast assembling of the tubes 12.

Figure 9:
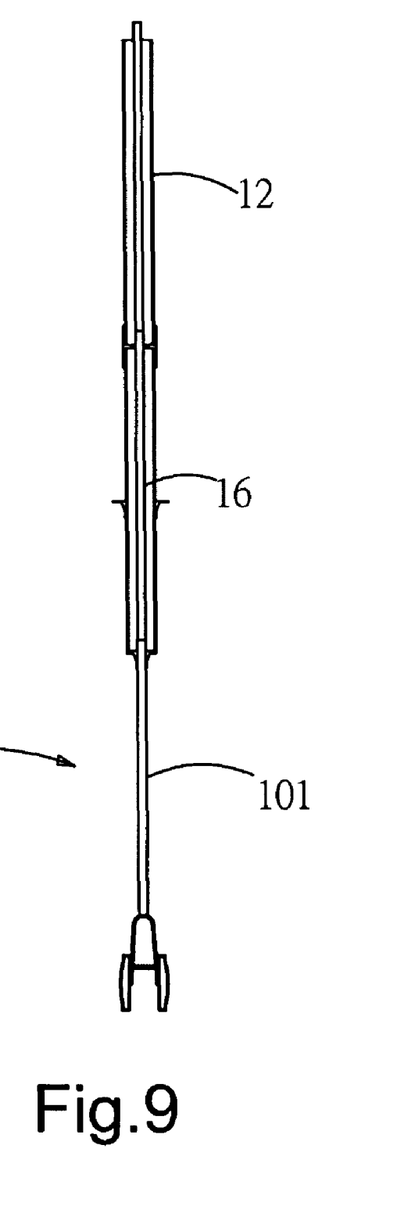
FIG. 9 is a schematic drawing showing structure of a further embodiment according to the present invention.

Refer to FIG. 9, a further embodiment is revealed. As shown in FIG. 8, the length of the tube 12 is increased. The difference between this embodiment and the one in FIG. 8 is in that length of the string 109 used to pull the sample stick 10 also increase along with increasing length of the tube 12. However, this leads to shaking and wiggle of the sample stick 10 and difficulties in turning back of the sample stick 10. Thus the handle 101 of the sample stick 10 is connected with at least one rod 16, instead of the string 109. Thus the problem in receiving of the sample stick 10 caused by shaking and wiggling is solved.

In summary, a sampling device for canisters according to the present invention provides an effective sampling method that increases accuracy of the contamination detection for canisters.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. A wipe sampling device of radioactive contaminants on surface of spent nuclear fuel storage canisters comprising:
    a tube;
    a sample stick disposed in the tube and one end thereof is disposed with at least one sampling paper; wherein the tube is set between a canister and a cask; when the sample stick moves forward, the sampling paper wipes the surface of the canister to take a sample, the sample stick comprising:
    a handle; and
    a sampling part disposed on one end of the handle and the sampling paper is set on the sampling part, wherein the sampling part comprising:
        a first sampling rack with a first fixed rack on one end thereof, opposite to an end connected with the handle; and
        a second sampling rack arranged on one side of the first sampling rack and having a second fixed rack on one end thereof, opposite to an end connected with the handle.

2. The device as claimed in claim 1, wherein one end of the sample stick is disposed with a string.

3. The device as claimed in claim 1, wherein a spring disposed between the first sampling rack and the second sampling rack.

4. The device as claimed in claim 1, wherein a rotation shaft is disposed between the first sampling rack and the first fixed rack.

5. The device as claimed in claim 1, wherein a rotation shaft is disposed between the second sampling rack and the second fixed rack.

6. The device as claimed in claim 1, wherein the first fixed rack fixes the sampling paper.

7. The device as claimed in claim 6, wherein an elastic member is arranged between the first fixed rack and the sampling paper.

8. The device as claimed in claim 1, wherein the second fixed rack fixes the sampling paper.

9. The device as claimed in claim 8, wherein an elastic member is arranged between the second fixed rack and the sampling paper.

10. The device as claimed in claim 1, wherein a projecting member is disposed on one end of the sample stick and a stopper is disposed on one end of the tube; when the sample stick travels, the projecting member rests against the stopper so as to stop the sample stick.

11. The device as claimed in claim 1, wherein the sampling device for canisters further comprising:
    a fixing ring is set outside the tube for fixing the tube between the canister and the cask.

12. The device as claimed in claim 1, wherein the tube is connected with at least one tube.

13. The device as claimed in claim 12, wherein the tubes are connected with each other by at least one connector.

14. The device as claimed in claim 1, wherein diameter of an opening on one end of the tube is larger than diameter of an opening on the other end of the tube.

15. The device as claimed in claim 1, wherein the handle is connected with at least one rod.

16. The device as claimed in claim 1, wherein the sampling device for canisters further comprising a spring sleeved around the handle and located over the sampling part.

* * * * *